United States Patent [19]
Thompson et al.

[11] Patent Number: 5,495,007
[45] Date of Patent: Feb. 27, 1996

[54] PHLOEM-SPECIFIC PROMOTER

[76] Inventors: Gary A. Thompson, 8445 E. Amethyst La., Tucson, Ariz. 85715; Brian A. Larkins, 1255 W. Chula Vista, Tucson, Ariz. 85704

[21] Appl. No.: 236,754

[22] Filed: Apr. 29, 1994

[51] Int. Cl.$^6$ .......................... C07H 21/04; C12N 15/82; C12N 15/29
[52] U.S. Cl. .......................... 536/24.1; 800/205; 536/23.6; 935/35; 435/172.3; 435/320.1
[58] Field of Search .................... 536/24.1, 23.6; 800/205; 935/35

[56] References Cited

U.S. PATENT DOCUMENTS

| | | | |
|---|---|---|---|
| 5,097,025 | 3/1992 | Benfey | 536/24.1 |
| 5,391,725 | 2/1995 | Coruzzi et al. | 536/24.1 |

OTHER PUBLICATIONS

Dannerhoffer et al. 1993 (May) Plant Physiology 102(1): 124(#702).
Bostwick et al. 1993 (May) Plant Physiology 102(1):73 (#402).
Wang et al 1994 (Jan.) Plant Molec. Biol. 24(1):159–170.
X. Liang, et al., "Developmental and environmental regulation of a phenylalanine ammonia–lyase–β–glucuronidase gene fusion in transgenic tobacco plants," *Proc. Natl. Acad. Sci. USA* 86:9284–9288, 1989.
H. Kononowicz, et al., "Subdomains of the Octopine Synthase Upstream Activating Element Direct Cell–Specific Expression in Transgenic Tobacco Plants," *The Plant Cell* 4:17–27, 1992.
P. Benfey, et al., "Combinatorial and synergistic properties of CaMV 35S enhancer subdomains," *The EMBO Journal* 9(6):1685–1696, 1990.
B. Keller, et al., "Vascular–Specific Expression of the Bean GRP 1.8 Gene Is Negatively Regulated," *The Plant Cell* 3:1051–1061, 1991.
M. Bhattacharyya–Pakrasi, et al., "Specificity of a promoter from the rice tungro bacilliform virus for expression in phloem tissues," *The Plant Journal* 4(1):71–79, 1993.
S. Kertbundit, et al., "In vivo random β–glucuronidase gene fusions in *Arabidopsis thaliana*," *Proc. Natl. Acad. Sci. USA* 88:5212–5216, 1991.
S. Medberry, "The Commelina Yellow Mottle Virus Promoter Is a Strong Promoter in Vascular and Reproductive Tissues," *The Plant Cell* 4:185–192, 1992.
N. Yang, et al., "Maize sucrose synthase–1 promoter directs phloem cell–specific expression of Gus gene in transgenic tobacco plants," *Proc. Natl. Acad. Sci. USA* 87:4144–4148, 1990.
J. Edwards, "Cell–specific expression in transgenic plants reveals nonoverlapping roles for chloroplast and cytosolic glutamine synthetase," *Proc. Natl. Acad. Sci. USA* 87:3459–3463, 1990.
D. Bostwick, et al., "Nucleotide Sequence of a Pumpkin Phloem Lectin cDNA," *Plant Physiol.* 102:693–694, 1993.
D. Bostwick, et al., "Pumpkin Phloem Lectin Genes Are Specifically Expressed in Companion Cells," *The Plant Cell* 4:1539–1548, 1992.
J. Cronshaw, et al., "Phloem Proteins," pp. 257–183, in *Sieve Elements*, H. D. Behnke and R. D. Sjolund Eds, Springer–Verlag, New York, 1990.
N. DeWitt, et al., "Evidence for a plasma membrane proton pump in phloem cells of higher plants," *The Plant Journal* 1(1):121–128, 1991.

*Primary Examiner*—Patricia R. Moody
*Attorney, Agent, or Firm*—Quarles & Brady

[57] ABSTRACT

A gene construct comprising SEQ ID NO:3, a phloem-specific promoter, and protein encoding nucleotide sequence not natively associated with SEQ ID NO:3 is disclosed. A gene construct comprising a protein encoding nucleotide sequence not natively associated with SEQ ID NO:3 and a sufficient portion of SEQ ID NO:3 such that the portion promotes the preferential expression of the protein-encoding nucleotide sequence in phloem tissue is also disclosed. A gene construct comprising a promoter sequence from a PP2-type gene isolated from a Cucurbita and a protein encoding sequence not natively associated with the promoter is disclosed.

5 Claims, 6 Drawing Sheets

```
-1882  TTTCTTGGAGTCATGCATCTTATATCGAATAAACATTTTGTCGATGTACGATGCCTGAGA
-1822  CAACGTTAGTGTTTTGTTCTTGTGATTCCGAACAATTTGTATTCCAAGAACAAACTGAGC
-1762  CTCTCCCAAAGCTTTCATTTGAAATTGTATCGCTAGCCAATGCTTAGTTGGAGTCAGAGC
-1702  TCGCACATCATTTCCAATGAGTAAGATATCGTCAACATACAACACTAGGAAAGCTACTGT
-1642  AGAGTTGACTATCATTTTATAAGACCAAGGTTGTCACATTCTATTCTTAAAGCCATAAGA
-1582  TGATCGCAGTATATATTAATGACATAACATGCTTATAATCTATGGGTGTATAAATCTCTTAC
-1522  TAATTAATTAATTTGTTTTTATGAGAATGAAATTAATTAAAATAAGTTCTCGAATTTTGAA
-1462  TAACTCATAATAACGCTAGAAAGCTAGAAAATAAAAATTTGTTAATTTATTAAAGATTTGTTTTAGAGATT
-1402  ATTAATAATAATTAATATATTAGGTATTTTTTTGTTAATTTATTAAAAATCAATCGTTGGAA
-1342  TTTACCATAGCCGGTTCAAGCACGGGAAAAAATTTGGGAGAAAATTCAATCGTTGGAA
-1282  GAGTTGAAGCTAATAAATTAAAATTAGCTACACTTTATTCGATATTTATTGTAAGATT
-1222  ACGTAACCTTTCGTGGTCAACAATATCTCCAAAATATTCTTTGAGATAATTCCAAATAA
-1162  AGATCATCACCACATTTATTTATTCTTATTAAAATAAGATCTTTCTATTTAAC
-1102  TTTCCTAAAGGAGAAAGTATCAAACATCACATTATCCAAGAAATTTTTATAAATTCTA
-1042  AGATTAAATTATTAAAATAGATATCCTTAAAAATCCATAGTCTAAATAAAACTCAAGC
-982   GTTCGAAGATGAGTAGTAACTTCAACAATGTACAATATCGACGAATAAATAACGGTAG
-922   AAAAAATTATAACTTTCAACAAATAACGTTCTAGTTTTATTTTTCGTGTCAAA
-862   TAGATTTTTTATTTAATATATATTTAATTTATTAACGAACAAAATATTATATTTAAT
-802   TAAGGTTTTAATTACAATATATGCTATTTCTATTAAAAATGGTTAATTATTTTCAAA
-742   ACACAAATATAAATGAAAAGGAAAATATATTTTTAAAAGAATTAAAATGTCTTTTCATT
-682   TCTTTTTACTTTTCTTTTCGGGCATCATGAACCGAAAATAATAGAACCTTCCTTTTAAGG
-622   CCTAAATAGTTCATATTCTAAATTAAATTCGTGTATTCTTAGATTTATATAAATAAAT
-562   TTCATAGACAAAATGCATTCATCCATACAAAACTTTCAAAACCGTTGGATTAATTC
-502   ATTTTCTTGAAGTAGTAAAATCTTTCAAAACTTCTCTACGACGGTAAAGTTAAAATGGAG
-442   TATTGGGGGTCGAAAAGGCAGGTTGAGCAATTGCAAGAACATCCATCTAGTTATAGCACA
-382   GCCAAAGTAGCATATACGACGACAAATAAAATTAGATATGATATATTTAATTAATATTATGTCTTGATTTTATAATTTT
-322   ACTTTTTAAATAAATAAATTAGATATAAAATAAAAAATATTGTTCTTGATTTTATAATTTT
-262   CAATTACTATTATTCATAATAAGTAAAAGGAATATATGAAAGAGGACGTTGATTTGTTAAAGAAGATAGA
-202   TAAAATCTTAAAGTAACGTAAAACAGTTCGGTATCAAATAGACATAGAGATAGACACGCGTATGA
-142   TTATTATGGACGTAAAACATGCTTAGGTTGAAAATAGTGCAGCAAATAGTGCAAAGAAGGGTTATATATA
-82    AAATAAGAAATAAGCATGCTTAGGTTGAAAATAGTGCAGCAAAGAAGGGTTATATATA

-22    TCCCTTCTTCCCTCTCACATTAACTCATATCTCACTTCTGTTCATAAAGAGAAGGCACTG
```

FIG. 2A

```
 39  CA ATG GAC AAC AAA GAG AAG GAA GCC AGA GAG AAA TTA GGA GGA GAA GTG AAG CTC GGT
        Met Asp Asn Lys Glu Lys Glu Ala Arg Glu Lys Leu Gly Gly Glu Val Lys Leu Gly

98  CAT TGC TTG GAT GTT ATT TTG AAG AAT GCT GAC GTA GCA CTG CAC TAT CCC TCC TTC CTT
     His Cys Leu Asp Val Ile Leu Lys Asn Ala Asp Val Ala Leu His Tyr Pro Ser Phe Leu

159  AAG CTT TAT GAC CAA CTT GTT GCT GGG ATC CTC TTG AAC AAG GGA GCT ATA GTAAGTGCAA
     Lys Leu Tyr Asp Gln Leu Val Ala Gly Ile Leu Leu Asn Lys Gly Ala Ile

219  CCATATATACTTCAACTCATTTACTCACCTTTGTATATCATAACCATATTAAATCAGAA

279  TATTGGCTTTCTTTCTTTACTTTGAATGCAG AAG TAC ATC TTT GAT AAG AAG TCA AAC AGC AAC
                                    Lys Tyr Ile Phe Asp Lys Lys Ser Asn Ser Asn

339  TGG TAC TTT ATA TTT GCA AGA GCT CTC TCA ATA GCT TGG ATT GAA GAT AAG AGA TAC TGG
     Trp Tyr Phe Ile Phe Ala Arg Ala Leu Ser Ile Ala Trp Ile Glu Asp Lys Arg Tyr Trp

399  AAA TGG GGA TCC TG GTATAATTTTTTAACTAATTTCTCAAGGGAAAAAATGATAAGAAC
     Lys Trp Gly Ser Cys

459  TTGATTCCTGATCTCTCTCACTCGGGTGTCTAAACACTTGCAG T GGC GAT AGC AAC GTT
                                                  Gly Asp Ser Asn Val

519  GCA GAG CTT ATT GAA GTA TCT TGG CTG GAC ATT CGT GGA AAG ATC AAC GAG TCT ATG CTC
     Ala Glu Leu Ile Glu Val Ser Trp Leu Asp Ile Arg Gly Lys Ile Asn Glu Ser Met Leu

579  TCA CAA AAT GTT GTG TAT GAG GTA GCA CTT CAG GTA CTG AAT AGT AGA GCC TCC GGG
     Ser Gln Asn Val Val Tyr Glu Val Ala Leu Gln Val Leu Asn Ser Arg Ala Ser Gly

639  TGG AAT GCT CCA CAA CTG AAC ATC GAG TTG AAG AAG CCA GAT GGG AGC AAG ATA GCG CAG
     Trp Asn Ala Pro Gln Leu Asn Ile Glu Leu Lys Lys Pro Asp Gly Ser Lys Ile Ala Arg Gln

699  GAA TGC CTG TTG GGG AAG CCA CAA AAC CAG TGG TTT GAG ATT GTT GAG TTC AAG GTA
     Glu Cys Leu Leu Gly Lys Pro Gln Asn Gln Trp Phe Glu Ile Val Val Glu Phe Lys Val

759  GGC AAC CAT GGC TGT GGA AGT AGC GGC GAG ATC GAG TTT TTT GCC TTT GAA CAT GGA GGG
     Gly Asn His Gly Cys Gly Ser Ser Gly Glu Ile Glu Phe Phe Ala Phe Glu His Gly Gly
```

FIG. 2B

```
819  CAT TGG AAG AGG GGG CTG CTC GTG AAA GGC GTT CGG ATT GGA GCA AAG GGA TGT GGT TGC
     His Trp Lys Arg Gly Leu Leu Val Lys Gly Val Arg Ile Gly Ala Lys Gly Cys Gly Cys

879  GCA TGA TCGAAATCCTCTCTCTCGAACTCAGACTACACTTATTTGATTTTGAGAGGCCA
     Ala ***
939  GAGTTTGTGTTATGATCCAATATGAAAAGAATGTACTAGCTTGCAAACATAAATAACAGC
999  ACCTTTGCTTACCGGCAATAAGGTCAAGTTTTAAATACATTTTGTTTTAGATACAATAA
1059 AATATACGTAATACTACTTTTTTTGGTTTACCAATCCGGGTAAGTATAAACACAGCAA
1119 ACAATTACGTGAAACTCGTATTGGTTCTCATGCTTCACCGACTTTTGGCTTACTA
```

FIG. 2C

Isolation of the 5' Flanking Region of gPC13-2E1
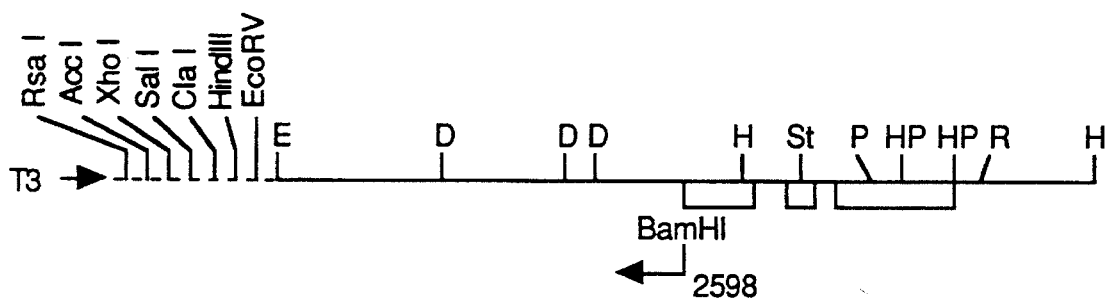
PCR Amplification Using T3 and 2598 Primers
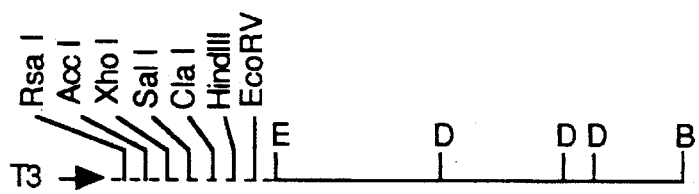
Digest with EcoRI and BamHI
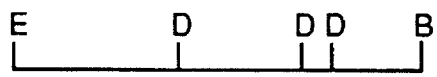
Insert the Fragment into EcoRI-BamHI of pBluescript KS+
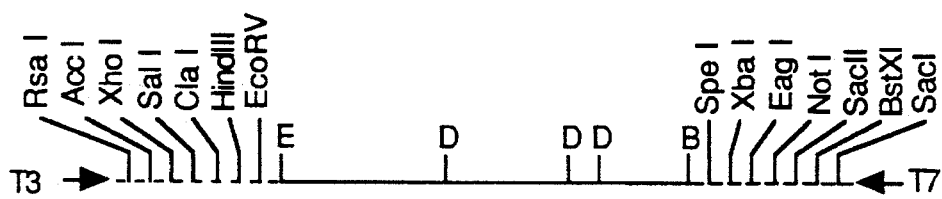
Digest with HindIII and BamHI
FIG. 3

PHLOEM-SPECIFIC PROMOTER

FIELD OF THE INVENTION

In general, the present invention relates to methods for creating a transgenic plant. Specifically, the present invention relates to methods of creating a transgenic plant using a tissue-specific promoter.

BACKGROUND

Phloem is an essential tissue for the long distance transport of photoassimilates. Sieve elements, highly specialized phloem cells, are the primary cells involved in long distance transport. P-proteins (phloem-proteins) are a major component of the cytoplasmic contents of sieve elements. P-proteins are synthesized very early in phloem ontogeny and persist in senescent sieve elements. Anatomical observations, combined with the physical characteristics of P-proteins, have led investigators to suggest that P-proteins may serve as wound sealing mechanism to prevent the loss of assimilates from disrupted sieve elements (Eschrich, W., in: *Transport in Plants I. Phloem Transport.*, M. H. Zimmerman and J. A. Milburn, Eds, pp. 39–56, 1975).

Biochemical characteristics of cucurbit P-proteins.

The phloem of many species within the family Cucurbitaceae is composed of large diameter sieve elements from which a protein-rich exudate can easily be collected. Two very abundant P-proteins in phloem exudates collected from Cucurbita species have been biochemically characterized: PP1 (phloem protein 1), a 96 kDa ($M_r$ 80-136 kDa) protein, and PP2 (phloem protein 2), a 48 kDa dimeric lectin (Beyenbach, et al., *Planta* 119:113–124, 1974; Kollman, et al., *Planta* 95:86–94, 1970; Read, et al., *Eur. J. Biochem.* 134:561–569, 1983). Both are basic proteins (pI 9.6–10.4) that have similar amino acid compositions (rich in Lys, Leu, Gly, Glx, Asx) and are components of phloem filaments in vivo (Beyenbach, et al., supra; Weber, et al., *Exp. Cell Res.* 87:79–106, 1974).

The PP1 monomers cross-link with one another by covalent disulfide linkages between cysteines, forming soluble polymers (Beyenbach, et al., *Planta* 119:113–124, 1974Read, et al., *Eur. J. Biochem.* 134:561–569, 1983; Sabnis, et al., *Planta* 145:459–466, 1979; Walker, Biochem. *Biophys. Acta* 257:433–444, 1972). Upon oxidation in vitro, purified PP1 formed distinct filaments and is considered to be the primary structural protein involved in the formation of slime plugs that are seen at sieve plates in electron micrographs of disrupted vascular tissues (Read, et al., *Eur. J. Biochem.* 134:561–569, 1983; Walker, *Biochem. Biosphys. Acta* 257:433–444, 1972; Walker, et al., *Ann Bot* 35:773–790, 1971). In the absence of thiol reagents, the large PP1 polymers will continue to cross-link forming an insoluble gel (Kleinig, et al., *Planta* 127:163–170, 1975).

PP2 is a lectin (hemagglutinin) that specifically binds poly(β-1,4-N-acetylglucosamine) or chitin (Allen, *Biochem. J.* 183:133–137, 1979; Beyenbach, et al., *Planta* 119:113–124, 1974; Read, et al., *Eur. J. Biochem.* 134:561–569, 1983; Sabnis, et al., *Planta* 142:97–101, 1978). The dimer was thought to be composed of two separate subunits, α (Mr 26,500) and β (Mr 25,000), joined by disulfide linkages between cysteine residues (Read, et al., *Eur. J. Biochem.* 134:561–569, 1983). Recent studies in our laboratory indicate that PP2 is a homodimer composed of similar subunits that may exhibit anomalous migration in SDS-PAGE. Purified PP2 remains soluble upon exposure to either atmospheric oxygen or oxidizing agents and is a component of phloem filaments due to covalent linkage to PP1 by means of disulfide bridges (Kleinig, et al., *Planta* 127:163–170, 1975; Read, et al., *Eur. J. Biochem.* 134:561–569, 1983; Read, et al., *Planta* 158:119–127, 1983).

P-protein filaments also may contain a third covalently-linked protein (Read, et al., *Eur. J. Biochem.* 134:561–569, 1983). This 45 kDa basic protein is much less abundant than the other P-proteins, and very little is known about the interactions of this protein with PP1 and PP2. The SDS-PAGE profile of cucurbit phloem exudate also contains 7–10 low molecular weight (lmw) polypeptides (9–20 kDa) that are not considered to be P-proteins (Read, et al., *Eur. J. Biochem.* 134:561–569, 1983). Recent findings in our laboratory suggest that some of the lmw proteins are coordinately synthesized with the abundant P-proteins.

Cucurbit phloem structure and P-protein accumulation.

Cucurbit phloem is composed of distinct types of phloem that are distinguished by their structure, origin and location in the stem (Crafts, *Plant Physiol.* 7:183–225, 1932). The Cucurbitaceae is one of several plant families that have bicollateral vascular bundles composed of internal and external phloem (fascicular phloem). A second feature that adds to the complexity of cucurbit phloem anatomy is the existence of extrafascicular phloem, which occurs in strands within the cortex and in arcs bordering both sides of the bundle (Blyth, Origin of primary extraxylary stem fibers in dicotyledons. *Univ. Cal. Berkeley Publ. Bot.* 30:145–232, 1958; Crafts, *Plant Physiol.* 7:183–225, 1932). In addition to the primary phloem, secondary phloem within the vascular bundle is derived from a vascular cambium. Long distance transport of assimilates is thought to occur in the sieve elements of the bicollateral vascular bundles and not in the extrafascicular phloem (Evert, et al., *Planta* 109:193–210, 1973).

P-protein accumulation during sieve element ontogeny in cucurbit stems has been described at the ultrastructural level (Cronshaw, et al., *J. Cell. Biol.* 38:25–39, 1968). In immature sieve elements, P-protein can be observed in the cytoplasm as small aggregates of fine fibrils that are intermixed with ribosomes, endoplasmic reticulum and dictyosomes.

In general, the P-protein bodies of the fascicular sieve elements disperse, whereas, the P-protein bodies of the extrafascicular sieve elements remain as aggregates. A recent report suggests that the changing environment within the sieve element, especially changes in osmotic potential, could be responsible for the dispersal of P-protein bodies into filamentous P-protein (Kulikova, *Soviet Plant Physiol.* 39:734–739, 1992).

Cucurbita leaves also have bicollateral vascular bundles. The abaxial phloem matures after the adaxial phloem and appears to be the primary pathway for transport of photoassimilates out of the leaf (Turgeon, et al., *Planta* 129:265–269, 1976). The adaxial phloem might transport assimilates to the expanding mesophyll tissues during leaf development when the leaf functions as a sink tissue (Turgeon, et al., *Planta* 129:265–269, 1976). During sieve element ontogeny, P-protein bodies accumulate in both the abaxial and adaxial phloem. In the mature abaxial sieve elements, most of the P-protein is filamentous and dispersed, whereas the P-protein bodies in the mature adaxial sieve elements remain condensed like in the extrafascicular phloem of the stem (Turgeon, et al., *Protoplasma* 83:217–232, 1975).

Promoters Active in Phloem Tissue

In recent years, transcriptional promoters have been identified that direct gene expression to the phloem. This is not surprising considering the central function of the phloem as the primary mechanism for long-distance transport within plants. However, in many cases gene expression that is directed by these promoters also occurs in other tissues.

Examples of promoters that direct vascular gene expression as part of their developmental program include regulatory sequences from viral (Benfey et al., *EMBO J.* 9[6] 1685–1696, 1990) and bacterial (Kononowicz et al., *Plant Cell* 4:17–27, 1992) genes as well as plant genes (Liang et al., *Proc. Natl. Acad. Sci. USA* 86:9284–9288, 1989); Keller and Baumgartner, *Plant Cell* 3:1051–1061). Transcriptional regulatory sequences have also been isolated from phloem-limited DNA viruses, such as the rice tungro virus (Bhattacharyya-Pakrasi et al., *Plant J.* 4[1] 71–79, 1993) and the commelina yellow mottle virus (Medberry et al., *Plant Cell* 4:185–192, 1992), that direct phloem-specific gene expression. In addition, the transcriptional regulatory elements of plant genes encoding proteins that have phloem-associated functions, such as sucrose synthase (Yang and Russell, *Proc. Natl. Acad. Sci. USA* 87:4144–4148, 1990), glutamine synthetase (Edwards et al., *Proc. Natl. Acad. Sci. USA* 87:3459–3463, 1990), and a phloem-specific isoform of the plasmamembrane H+-ATPase (DeWitt et al., *Plant J.* 1[1]: 121–128, 1991), have been shown to direct phloem-specific expression of reporter genes in transgenic plants.

SUMMARY OF THE INVENTION

The present invention is a gene construct comprising SEQ ID NO:3 and a protein-coding nucleotide sequence that is not natively associated with SEQ ID NO:3.

In another embodiment, the present invention is a gene construct comprising a protein-coding nucleotide sequence not natively associated with SEQ ID NO:3 and a sufficient portion of SEQ ID NO:3 such that the portion actuates the preferential expression of the protein-coding nucleotide sequence in phloem tissue.

In another embodiment, the present invention is a gene construct comprising a protein-coding sequence not natively associated with SEQ ID NO:3 and a promoter sequence sufficiently homologous to SEQ ID NO:3 such that the sequence provides preferential expression in phloem tissue.

The present invention is also a gene construct comprising a protein-coding sequence not natively associated with SEQ ID NO:3 and a promoter sequence from a PP2-type gene isolated from a member of Cucurbita species, said promoter sequence sufficient to effect gene expression preferentially in phloem tissue.

It is an object of the present invention to provide a promoter useful in gene expression.

It is another object of the present invention to provide a promoter capable of providing preferential expression in phloem tissue.

It is another object of the present invention to provide SEQ ID NO:3.

It is another object of the present invention to provide a promoter sequence isolated from a PP2-type gene. It is another object of the present invention to provide a sufficient portion of SEQ ID NO:3 such that preferential expression in tissue is obtained. It is an advantage of the present invention that a transgenic plant may be created in which the transgene is expressed preferentially in phloem tissue. Other objects, features and advantages of the present invention will become apparent after examination of the specification, claims and drawings.

DESCRIPTION OF THE DRAWING

FIG. 2A is the nucleotide sequence of gPC13-1a from nucleotide–1882 to +38.

FIG. 2B is the nucleotide and deduced amino acid sequence of gPC13-1A from nucleotide 39 to 818.

FIG. 2C is the nucleotide and deduced amino acid sequence of gPC13-1A from nucleotide 819 to 1173.

FIG. 3 is a flow diagram of the creation of a truncated version of the gPC13-2E1 promoters.

DESCRIPTION OF THE INVENTION

In General

Figure 1:
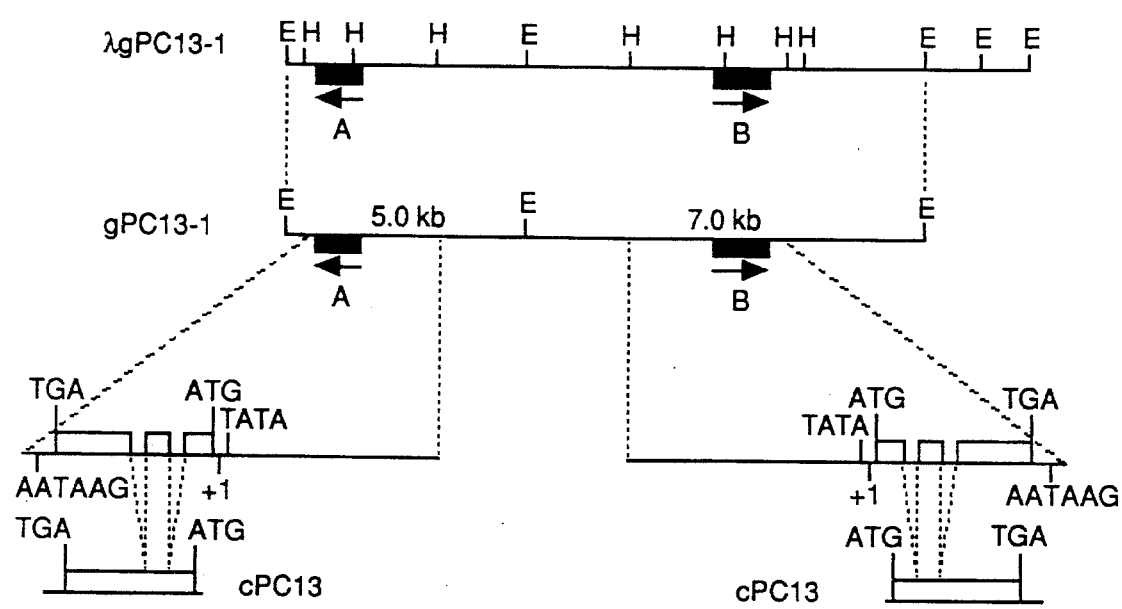
FIG. 1 is a partial restriction map of λgPC13-1.

We have isolated a nucleotide sequence, SEQ ID NO:3, capable of conferring phloem tissue specific expression when connected to a protein-encoding nucleotide sequence. Our isolation of SEQ ID NO:3 from a pumpkin gene that expresses the phloem-specific PP2 protein is described below in detail in the Examples. The present invention is a gene construct containing either SEQ ID NO:3 or a portion or version of SEQ ID NO:3 sufficient to effect preferential expression of a transgene in plant phloem cells. The present invention is also a gene construct containing a promoter sequence isolated from a PP2-type gene.

It is an advantage in creating transgenic plants to be able to direct the expression of a transgene to a targeted tissue. In some cases, constitutive expression of a transgene can lead to plant abnormalities or loss of plant vigor. We anticipate that targeted gene expression will lead to more effective control of a phloem-limited virus. Coat protein genes as well as other viral genes (i.e., replicase) are good examples of transgenes that might benefit from phloem-specific expression. Also, genes encoding proteins that may control phloem-feeding insects (such as aphids and whiteflies) would be good candidate genes. Another group of genes that might benefit from phloem-specific expression are genes whose encoded proteins function in phloem-related activities such as sugar transport and synthesis and amino acid transport and synthesis.

A promoter of the present invention will confer preferential expression of a protein-encoding nucleic acid sequence in phloem tissue. By "preferential expression in phloem tissue" or "phloem-specific expression" we mean that the gene sequence is expressed significantly more in phloem than in other tissue types.

Gene Construct

The present invention requires that the promoter sequence be combined with a protein-coding sequence in a gene construct. Commonly used methods of molecular biology well-known to those of skill in the art may be used to manipulate the DNA sequences.

By "gene construct" we mean any of a variety of ways of combining the promoter sequence with the protein-encoding sequence in a manner that operably connects the promoter sequence with the protein-encoding sequence. Typically, the promoter sequence will be 5' or "upstream" of the protein-encoding sequence.

For example, these two sequences may be combined together on a plasmid or viral vector. Other functional sequences, such as secretion signals, polyadenylation and termination sequences, may be added to the gene construct. Alternatively, the protein-encoding and promoter sequences may be combined together with only other needed functional sequences and used without a vector.

By "protein encoding sequence" we mean any nucleotide sequence capable of expression at the mRNA level. The mRNA may in turn be expressed as a protein or not. The protein encoding sequence may be in either the sense or antisense orientation. The antisense orientation would be useful to express antisense mRNA.

A suitable protein encoding sequence will not be associated with the promoter sequence in nature. For example, because the PP2 coding sequence is naturally associated with SEQ ID NO:3, PP2 in its native form is not a suitable protein encoding sequence.

SEQ ID NO:3 and Variants

SEQ ID NO:3 is described below. There are several methods commonly known to those of skill in the art of molecular biology of obtaining this sequence. For example, one may create nucleic acid probes from the known sequence and use these probes to screen a pumpkin genomic library to obtain the entire sequence. Alternatively, one may synthetically create the sequence. One could also isolate the PP2 protein, raise monoclonal or polyclonal antisera and probe a cDNA expression library. Once one had obtained the PP2 cDNA, one could screen a genomic library for the promoter sequence. One could also isolate the protein, obtain a portion of the primary amino acid sequence and design degenerate synthetic oligonucleotide probes.

The Examples below disclose that SEQ ID NO:3 is sufficient to confer preferential expression of a protein encoding sequence in phloem tissue. However, we envision that SEQ ID NO:3 could be truncated and still confer the same properties. We do not know which specific deletions would be successful. However, one skilled in the art of molecular biology would be able to take SEQ ID NO:3 and perform deletional analysis experiments to determine what portion of SEQ ID NO:3 is essential to confer phloem-specific expression. One could create a genetic construct with the candidate deletion mutations and a protein-encoding sequence and perform experiments with transgenic plants as described below in the Examples. Occurrence of the test protein sequence preferentially in phloem indicates a successful deletion mutant. In this manner, one could determine which parts of SEQ ID NO:3 are essential for tissue-specific transcription.

One skilled in the art of molecular biology would appreciate that minor deletions, additions and mutations may not change the attributes of SEQ ID NO:3. Many of the nucleotides of SEQ ID NO:3 are probably not essential for its unique function. To determine whether or not an altered sequence has sufficient homology with SEQ ID NO:3 to function identically, one would simply create the candidate mutation, deletion or alteration and create a gene construct including the altered sequence and a protein-encoding sequence. This gene construct could be tested as described below in the examples for the occurrence of the test protein predominantly in phloem tissues in a transgenic plant.

The present invention is also a gene construct containing a promoter sequence isolated from a PP2-type gene. The examples below demonstrate that PP2 mRNA is found in a wide variety of Cucurbita species. Therefore, we believe that all members of Cucurbita probably contain a PP2-type gene. (By "PP2-type gene" we mean a gene containing a sequence encoding the PP2 protein.)

To obtain a PP2-type gene promoter from a Cucurbita, one would most easily begin by obtaining a probe constructed from a sequence within the coding region of SEQ ID NO:1. This probe could be used to screen a genomic library isolated from another member of Cucurbita, such as squash or gourd. Standard methods known to those of skill in the art of molecular biology would enable one to determine the parameters of the coding region for PP2 and, thus, the parameters of the promoter. In this manner, one would isolate an analogous promoter to SEQ ID NO:3 in another member of the Cucurbitaceae family.

EXAMPLES

Characterization of Molecular Probes

Characterization of cDNA clones.

To obtain cDNA clones corresponding to PP1, PP2, and additional pumpkin P-proteins, we raised polyclonal antibodies in chickens against total reduced proteins from pumpkin phloem exudate. A complex antiserum was obtained that reacts with many of the phloem exudate proteins resolved by SDS-PAGE. To determine if the antiserum was specific for phloem exudate proteins, we tested it for cross-reactivity with proteins isolated from pumpkin callus tissue. Although callus tissue contains a large number of abundant proteins, the antiserum cross-reacted with only a single protein band. This protein has the mobility of PP1 and may reflect PP1 synthesis in differentiating phloem cells within the callus because P-proteins have previously been observed in differentiating sieve elements in squash callus tissue. The absence of cross-reactivity between the antiserum and proteins from callus tissue reflects the antiserum's specificity for the phloem exudate proteins. The preimmune serum did not cross-react with proteins from pumpkin phloem exudate or pumpkin callus.

To identify mRNAs corresponding to phloem proteins, an expression cDNA library was constructed with poly(A)$^+$ RNA isolated from pumpkin seedlings. This library was screened with the phloem protein antiserum and 22 immunopositive plaques were obtained. The 10 most immunoreactive phages were selected for further analysis. To determine if these 10 clones represented unique or related sequences, we excised the pBluescript SK-plasmid containing each cDNA from the λ ZAP clone, purified the DNA, and performed a cross-hybridization analysis. The results of these experiments showed that the 10 cDNAs represented two groups of closely related or identical sequences. Clones with the largest cDNA inserts were selected for detailed analysis and were designated cPC7 (1.38 kb) and cPC13/20 (cPC13 is 980 bp and cPC20 is 792 bp).

We found that beta-galactosidase fusion proteins encoded by three cDNA clones were immunologically related to either PP1 (cPC7) or PP2 (cPC13 and cPC20). The nucleotide sequence for the two PP2 cDNAs, cPC13 (868 bp) and cPC20 (792 bp), were identical and encoded a complete open reading frame (ORF) of 654 nucleotides. The deduced protein was 218 amino acids in length and had a calculated molecular weight of 24,478 daltons which corresponded to the apparent molecular weight of approximately 25–26.5 kDa reported for PP2 subunits (Read, et al., *Eur. J. Biochem.* 134:561–569, 1983). The deduced amino acid composition also corresponded with experimentally determined amino acid compositions that were reported by other laboratories (Allen, *Biochem. J.* 183:133–137, 1979; Beyenbach, et al., *Planta* 119:113–124, 1974) and confirmed by our laboratory. We verified that cPC13/20 encoded the PP2 chitin-binding lectin by a functional demonstration of carbohydrate-binding specificity of the recombinant protein.

The PP1 cDNA, cPC7 (1380 bp), hybridized to a mRNA of approximately 2500 nucleotides indicating that the clone is a partial cDNA. Analysis of the nucleotide sequence of cPC7 revealed an incomplete ORF of 1260 nucleotides encoding a deduced polypeptide of 420 amino acids. The incomplete polypeptide is composed of two similar regions (I and II) that are 196 amino acids and 201 amino acids, respectively. Each of these regions is composed of two subregions, A (103 amino acids) and B (72 amino acids), that are separated by 20 (I) and 25 (II) unique amino acids. IA and IIA have a 78% identity in the amino acid sequence and 86% identity in the nucleic acid sequence. IB and IIB are less similar with 51% identity in the amino acid sequence and 72% in the nucleic acid sequence. The decrease in amino acid identity is due to point mutations and small deletions in the nucleotide sequence.

Genomic Organization of Phloem Lectin Genes

Mapping and sequence analysis of PP2 genomic clones.

We obtained three genomic clones, λgPC13-1 λgPC13-2, and λgPC13-12 by screening a pumpkin genomic library with the PP2 cDNA, cPC13. The partial restriction maps of the genomic DNA inserts of λgPC13-2 and λgPC13-12 were extremely similar in their arrangement and appeared to represent the same gene. Southern blots of HindIII digested genomic DNA showed that a 1.3 kb HindIII fragment and an additional 1.1 kb HindIII fragment hybridized to the cDNA probe. Analysis of the third genomic clone, λgPC13-1, showed that this clone contained both the 1.3 kb and 1.1 kb HindIII hybridizing fragments. Detailed restriction mapping analysis confirmed that λgPC13-1 contains two contiguous PP2 genes (A and B) that are located in opposite orientations and separated by approximately 7 kb (FIG. 1).

Referring to FIG. 1, the genomic clone λgPC13-1 contains two genes encoding PP2 (solid boxes) that are transcribed in opposite directions (marked by arrow). The transcription initiation site is denoted by +1. The translation initiation methionine codon, stop codon, and polyadenylation sequence are labeled as ATG, TGA, and AATAAG, respectively. The exons of PP2 in cPC13 are marked by crosshatched boxes. "H" indicates a HindIII site. "E" indicates an EcoRI site.

Sequence comparison of the A and B genes of λgPC13-1 and the gene encoded by λgPC13-2 revealed that the genes encoding PP2 in *C. maxima* were highly conserved. The entire 2563 nucleotide sequence of gPC13-2E1 was identical to the gPC13-1A gene from nucleotides −1118 to +1445. Mapping, sequence, and genomic DNA blot data suggested that gPC13-2, gPC13-12, and gPC13-1A were clones of the same gene. The nucleotide sequence of the two contiguous genes, A (3466 bp) and B (3295 bp), encoded by λgPC13-1 was 99.8% identical over a region of 3055 bp.

The nucleotide sequences further 5' and 3' of this region were divergent with 24% and 26% identity, respectively. The conserved region included 1922 bp of 5' flanking region that contained 4 nucleotide differences between the A and B genes (−1870, A/C; −1818, G/A; −1712, G/C; −1700, G/C) and 289 bp of 3' flanking region that contained a single nucleotide difference (+1065, G/A) between the genes.

FIGS. 2A–C show is the nucleotide and deduced amino acid sequence of gPC13-1A. As mentioned above, the sequence of gPC13-1B differs at four nucleotides in the 5' region and one nucleotide in the 3' region. SEQ ID NOs:1 and 2, below, are the nucleotide and protein sequences (respectively) of FIGS. 2A–C.

The protein coding regions for both A and B genes were identical to each other and to the PP2 cDNAs. In the genomic clones the three exons (168 bp, 107 bp, 389 bp) of the PP2 coding region were interrupted by two introns. Intron I extended 97 bp from nucleotide +209 to +305 and intron II extended 90 bp from nucleotide +413 to +502. Each intron was flanked by the dinucleotide sequences 5' GT . . . AG-3' which are typical of genes transcribed by RNA polymerase II.

The transcription initiation site was identified 40 bp 5' of the translation initiation codon (ATG) by S1 nuclease digestion and confirmed by primer extension analysis. A putative TATA box (TATATATA) was identified 30 bp 5' of the transcription initiation site (+1). The 3' flanking sequences of each clone contained a putative polyadenylation signal sequence (+1016, AATAAG) and sequences corresponding to the 3' end of the PP2 cDNAs were located within the region of identity.

P-protein genes are conserved in Cucurbita species. Proteins isolated from phloem exudates of different genera within the Cucurbitaceae show a large degree of heterogeneity in their composition and abundance (Sabnis, et al., *Planta* 145:459–466, 1979). To determine the conservation of PP1 and PP2 within the genus we have examined other Cucurbita species for the presence of PP1 and PP2, their mRNAs and the genes that encode them. The species we tested were *C. maxima* (cv Big Max), *C. maxima* (cv Hubbard), *C. moschata* (cv Butternut), *C. pepo* (cv Zucchini), *C. pepo* (cv Crookneck), *C. argyrosperma*, *C. argyrosperma* ssp *sororia*, *C. digitata*, *C. ecuadorensis*, *C. foetidissima*, *C. lundelliana*, and *C. martinezii*.

Genomic DNA blot analysis showed that PP1 and PP2 genes were present in all tested Cucurbita species. The nuclear DNA content of the 10 Cucurbita species was determined by flow cytometry and was used to estimate the number of PP2 genes in their respective genomes. Copy number reconstructions of the 10 Cucurbita species indicated that within some species PP2 was encoded by a small gene family of 3-8 genes, whereas in others PP2 is encoded by a single gene or duplicate genes. The latter appears to be the case for *C. maxima* cv. Big Max, and the two identical genes within λgPC13-1 were indicative of the gene duplication event.

The conservation of PP2 among Cucurbita species was also examined at the RNA and protein level. RNA blot analysis of all tested Cucurbita species showed single transcript size of approximately 1000 nucleotides for PP2. Interestingly, we observed that 7 species, including *C. maxima*, showed a single polypeptide when PP2 was affinity purified from phloem exudates. However, 4 species show two polypeptides, both of which react with the PP2 specific antibodies. This suggests that PP2 exists in some species as a homodimer. Our results are in contrast to the findings of Read and Northcote (Read, et al., *Eur. J. Biochem.* 134:561–569, 1983) who reported that the PP2 dimer of *C. maxima* is composed of two subunits, α(Mr 26,500) and β(Mr 25,000).

We have examined affinity-purified PP2 from 35 different *Cucurbita maxima* accessions, including the cultivar Golden Delicious that was used by Read and Northcote, and have not been able to replicate their findings within this species. These analyses do not discount the possibility of post-translational modification or conformational differences resulting in PP2 isoforms. We have concluded that within *C. maxima* PP2 is encoded by two identical genes that are closely linked and that the protein is a homodimer.

In contrast, the PP2 subunits in *C. argyrosperma* are clearly two polypeptides. Reverse transcriptase PCR (RT-PCR) of the PP2 protein coding region using total RNA isolated from *C. argyrosperma* and primers based on the sequence of cPC13/20 resulted in a single-sized PCR product. Restriction mapping with enzymes that are diagnostic for *C. maxima* clones revealed two cDNAs (Arg2, Arg5)

with different restriction patterns. Nucleotide sequence comparison of the two cDNAs showed 97.3% identity and a deduced amino acid sequence identity of 93.5% Nucleic acid sequence comparison with cPC13 from *C. maxima* showed 91% identity for both clones. The calculated molecular weights for both clones (Arg2=24,361; Arg5=24,526) were similar.

Analysis of P-Protein Gene Expression and Protein Stability

Steady state PP1 and PP2 mRNA accumulation.

To compare PP1 and PP2 mRNA accumulation, we analyzed total RNA isolated from hypocotyl tissue of pumpkin seedlings by RNA blot and dot blot analysis. The pattern of PP2 expression for the first 10-12 days after germination (DAG) was similar to that reported by Sham and Northcote (Sham, et al., *Planta* 170:392–399, 1987). PP2 mRNA was initially detected at 3 DAG and increased over the next 7 days to a maximum of approximately 0.05% of total RNA at 10 DAG. At 10 DAG the hypocotyl reached approximately 90 percent of its total length. In contrast to previous reports of rapid decreases in PP2 mRNA within three days after maximal accumulation, our analysis showed PP2 mRNA gradually declined over the next 12–14 days. Large unexplained fluctuations in PP2 mRNA resembling the data presented by Sham and Northcote were detected over several time points in some experiments; however, extending the analysis for a total of two weeks clearly revealed the overall pattern of PP2 mRNA accumulation. Although the steady-state level of PP2 mRNA declined after 10–12 DAG, the amount of PP2 mRNA at 24 DAG was approximately 25% of the maximal level. The pattern of PP1 mRNA accumulation paralleled PP2 mRNA, but at levels 5 to 7 times lower than PP2 mRNA. Anatomical evidence presented below supports the observation that the accumulation of PP1 and PP2 mRNA reflects the development of the vascular tissue during the period of hypocotyl elongation. We speculate that PP1 and PP2 mRNAs are synthesized over a prolonged period as a function of sieve element maintenance and during the development of secondary phloem.

We also examined PP1 and PP2 mRNA accumulation within different plant organs at 24 DAG. The relative amounts of PP1:PP2 mRNA in the different organs were consistent with the results obtained from the hypocotyl. Dot blot analysis showed that PP2 mRNA accumulation was highest in stem tissue (internode) ranging from 0.05–0.06% of the total RNA. Within leaves, PP2 mRNA accumulation varied within leaf parts (petiole vs. lamina) and leaf developmental stages. The petioles of the first three leaves had relatively high levels of PP2 mRNA ranging between 0.01–0.02% of the total RNA, whereas PP2 mRNA isolated from the fourth leaf petiole was expressed at very low levels ($8\times10^{31\ 4}$% of total RNA). PP2 mRNA accumulated in the leaf lamina of all four leaves and in the shoot-tip to levels that were only slightly above background and similar to the fourth leaf petiole. Leaf growth data showed the first three leaves were almost fully expanded while the fourth leaf was well below 50% expansion.

Correlation of P-protein expression and phloem development.

Results from the mRNA accumulation analysis suggested that the hypocotyl would be an appropriate tissue in which to investigate the expression and interactions of PP1, PP2, and their mRNAs during phloem development. An anatomical study of developing hypocotyl tissue (0–24 DAG) showed all stages of phloem development. During the first two days of seedling growth when PP1 and PP2 mRNA are not detectable, the vascular tissue of the hypocotyl consists of primarily procambial bundles containing few differentiated protoxylem and protophloem elements.

By 3 DAG when PP1 and PP2 mRNA accumulation were first detected in the hypocotyl, the vascular bundles had increased in size and obtained the structure the bundles would have throughout the rest of plant growth. Individual bundles had developed so that the internal and external phloem portions of the bundle could be recognized. The differentiating metaxylem was separated from the differentiating external metaphloem by the incipient vascular cambium. The extrafascicular arcs adjacent to the bundle were also differentiating sieve elements. However, initiation of the extrafascicular elements within the cortex had just begun.

By 6 DAG when PP1 and PP2 mRNA accumulation had increased substantially, the vascular bundles were well developed with abundant metaphloem and metaxylem elements. In addition, the first secondary elements were differentiating from the vascular cambium. At this stage, the bundle looked very similar to all later stages in the developmental series we examined. Maximum PP1 and PP2 mRNA accumulation occurred at 10 DAG when the primary phloem was fully mature and the secondary phloem was differentiating. This coincided with the cessation of hypocotyl elongation.

In addition, observations on expanding hypocotyls showed a developmental sequence of PP2 mRNA accumulation. In the youngest hypocotyls, accumulation was skewed with the majority of transcripts occurring in the lowest segment. This correlated with seedling development, where the basal portion of the hypocotyl was oldest. As the hypocotyl continued to elongate, the distribution of PP2 mRNA accumulation in the segments reflected differences in the development of the vascular tissue from base to apex. When the hypocotyl had fully elongated, the level of PP2 mRNA in all hypocotyl segments was fairly uniform.

Localization of P-protein Gene Expression

In situ localization of PP1 and PP2 mRNA in companion cells.

To obtain evidence of the site of P-protein synthesis, we localized PP1 and PP2 mRNA by in situ hybridization. Cross-sections of pumpkin hypocotyl tissue were incubated with in vitro synthesized transcripts labeled with digoxigenin-11-UTP. By using this non-isotopic labeling method, we achieved high spatial resolution of the signal with retention of tissue morphology. The localization pattern for PP1 and PP2 was identical. PP1 and PP2 antisense transcripts hybridized to mRNA within the phloem of hypocotyl tissues in both the bundle and extrafascicular phloem tissue. Additionally, the extrafascicular phloem strands within the cortex were often labeled. PP1 and PP2 mRNA was localized only in companion cells within both bundle and extrafascicular phloem. Smith, et al. (Smith, et al., *Planta* 170:461–470, 1987) immunocytochemically localized PP2 to the sieve elements and companion cells of the mature phloem. Since most of the major organelles, including ribosomes, degenerate during the maturation of the sieve element, P-protein synthesis is thought to occur either in the immature sieve elements or in the companion cells prior to transport into the sieve element.

The PP2 promoter directs phloem-specific. GUS expression in transgenic plants. We have generated transgenic tobacco plants containing the GUS reporter gene under the transcriptional regulation of PP2 promoter sequences. We inserted 1151 bp of 5' flanking sequence from the PP2 genomic clone gPC13-2E into the polylinker region of pBI101.1 (Jefferson, et al., *EMBO J.* 6:3901–3907, 1987). FIG. 3 describes the creation of this 1151 bp region. SEQ ID NO:3, below, describes this region.

Referring to FIG. 3, the gPC13-2E1 clone is used as a PCR template using T3 and 2598 primers. The T3 primer sequence was made for us from the sequence of the Bluescript plasmid vector. The 2598 primer was designed from the sequence of gPC13-2E1 and was modified to include a BamHI restriction site for subcloning into pBI101. The PCR amplification product was digested with EcoRI and BamHI and inserted into the EcoRI-BamHI site of pBluescript KS+ (Stragene Cloning Systems, La Jolla, Calif.). The segment was then digested with HindIII and BamHI. This HindIII/BamHI segment extends from nucleotides −1118 to +32 and includes the transcription start site as well as most of the untranslated leader sequence. In FIG. 2, this segment is indicated by heavy vertical lines.

Figure 4:
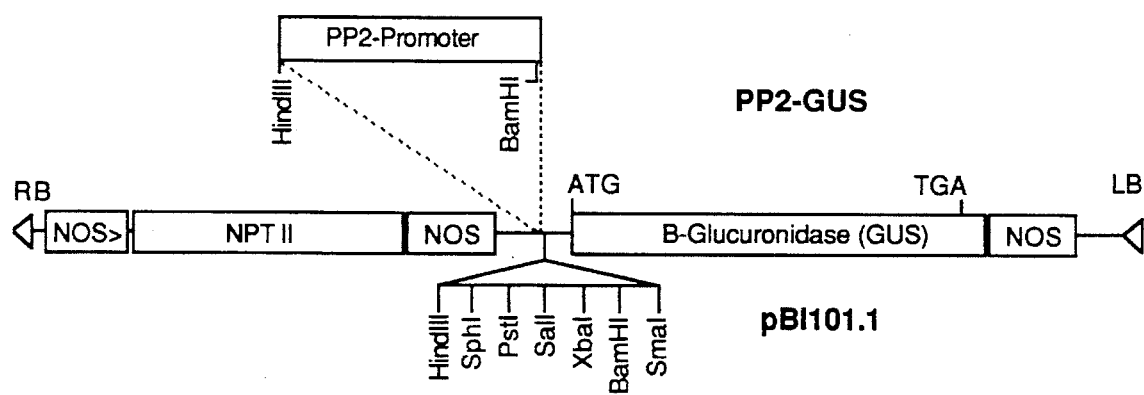
FIG. 4 is a diagram of the gPC13-2E1 HindIII/BamHI fragment linked to the β-glucuronidase gene in pBl101.1.

FIG. 4 is a diagram of the HindIII/BamHI fragment positioned in front the β-glucuronidase (GUS) gene. The HindIII/BamHI segment was transformed into tobacco plants by the following method:

Constructs in the binary vector were mobilized from the E. coli strain DH5α into the Agrobacterium tumefaciens strain LBA4404 by triparental mating. Transformation of the Nicotiana tabacum line Wisconsin 38 was carried out by the leaf disk method (Horsch, et al., Science 227:1229–1231, 1985). Forty independently regenerated kanamycin-resistant plants tested positive for β-glucuronidase activity. The total number of plants tested was 62. We did not determine if the plants that were not positive for GUS contained the gene and were not expressing GUS or if they were escapes (did not contain the gene).

We have histochemically localized GUS activity to the phloem of the 40 transgenic tobacco plants. Our histochemical staining indicates that the sequences do not appear in parts of plant tissue that do not contain phloem. These data demonstrate that the promoter is functional, tissue-specific, and works across species.

We claim:

1. A gene construct comprising SEQ ID NO:3 and a protein encoding nucleotide sequence not natively associated with SEQ ID NO:3.

2. A gene construct comprising a protein encoding nucleotide sequence not natively associated with SEQ ID NO:3 and a sufficient portion of SEQ ID NO:3 such that the portion promotes the preferential expression of the protein encoding nucleotide sequence in phloem tissue.

3. A gene construct comprising a protein encoding sequence not natively associated with SEQ ID NO:3 and a promoter sequence sufficiently homologous to SEQ ID NO:3 such that the sequence promotes preferential expression of the protein encoding sequence in phloem tissue.

4. A gene construct comprising a promoter sequence from a gene encoding a PP2 protein isolated from a Cucurbita, said promoter sequence sufficient to effect gene expression preferentially in phloem tissues and a protein encoding sequence, the promoter not natively associated with the protein encoding sequence.

5. The construct of claim 4 wherein the Cucurbita is selected from the group consisting of *C. maxima* (cv Big Max), *C. maxima* (cv Hubbard), *C. moschata* (cv Butternut), *C. pepo* ( cv Zucchini ), *C. pepo* ( cv Crookneck ), *C. argyrosperma*, *C. argyrosperma* ssp *sororia*, *C. digitata*, *C. ecuadorensis*, *C. foetidissima*, *C. lundelliana*, and *C. martinezii*.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 3055 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:1:

```
TTTCTTGGAG  TCATGCATCT  TATATCGAAT  AAACATTTTG  TCGATGTACG  ATGCCTGAGA     60
CAACGTTAGT  GTTTTGTTCT  TGTGATTCCG  AACAATTTGT  ATTCCAAGAA  CAAACTGAGC    120
CTCTCCCAAA  GCTTTCATTT  GAAATTGTAT  CGCTAGCCAA  TGCTTAGTTG  GAGTCAGAAA    180
TCGCACATCA  TTTCCAATGA  GTAAGATATC  GTCAACATAC  AACACTAGGA  AAGCTACTGT    240
AGAGTTGACT  ATCATTTTAT  AAACACAAGG  TTGTCACATT  CTATTTAAAG  CCATAAGATT    300
TGATCGCAGT  ATATATTAAT  GGACATAACA  TGCTCTATAA  AATTGATTGA  TTGAAGAGTT    360
TAATTAATTA  ATTTTGTTTT  ATGAGAGCTT  ATAATCTATG  GGTGTATAAA  ATCTCTTTAC    420
TAACTCATAA  TAACGCTAGA  AAGAATGAAA  TTAATTAAAA  TAAGTTCTCG  AATTTTTGAA    480
ATTAATAATT  AATATATTAG  GTATTTTTTT  GTAATTTATT  AAAGATTTTG  TTTAGAGATT    540
TTTACCATAG  CCGGTTCAAG  CACGGGAAAA  AATTTTGGGG  AGAAAATTCA  ATCGTTGGAA    600
GAGTTGAAGC  TAATAAATTA  AAAATTAGCT  ACAACTTTAT  TCGATATTTA  TTGTAAGATT    660
ACGTAACCTT  TCGTGGTCAA  CAATATCTCC  AAAATATTCT  TTTGAGATAA  TTCCAAATAA    720
AGATCATCAC  CACATTTATT  TAATTTATTC  TTTATATTAA  ATAAGATCTT  TCTATTTAAC    780
TTTCCTAAAG  GAGAAAGTAT  CAAACATCAC  ATTATCCAAG  AAATTTTTTT  ATAAATTCTA    840
AGATTAAATT  TATTAAAAAT  AGATATCCTT  AAAAATCCAT  AGTCTAAATA  AAACTCAAGC    900
GTTCGAAGAT  GAGTAAATAA  ATGTGATTAA  TGTACAATAT  CGACGAATAA  ATAACGGTAG    960
AAAAAAATTA  TAACTTTCAA  CAAATAACT   GTTCTAGTTT  TATTTTTTTC  GTGTGTCAAA   1020
TAGATTTTTT  ATTTAATATA  TATTTTTTAA  TTTATTAACG  AACAAAATAT  TATATTTAAT   1080
TAAGGTTTTA  ATTACAATAT  ATGCTATTTT  CTATTAAAAA  ATGGTTAATT  ATTTTTCAAA   1140
```

| | | | | | |
|---|---|---|---|---|---|
| ACACAAATAT | AAATGAAAAG | GAAATATAT | TTTTTAAAAG | AATTAAAATG | TCTTTTCATT | 1200 |
| TCTTTTACTT | TTCTTTTCGG | GCATCATGAA | CCGAAAATAA | TAGAACCTTC | CTTTTTAAGG | 1260 |
| CCTAAATAGT | TCATATTCTA | AATTAAATTC | GTGTATTCTT | AGATTATAT | AAAAATAAAT | 1320 |
| TTCATAGACA | AAATGCATTC | ATCCATACAA | AATAATTAAA | AACAACCGTT | GGATTAATTC | 1380 |
| ATTTTCTTGA | AGTAGTAAAA | TCTTTCAAAA | CTTCTCTACG | ACGGTAAAGT | TAAAATGGAG | 1440 |
| TATTGGGGGT | CGAAAAGGCA | GGTTGAGCAA | TTGCAAGAAC | ATCCATCTAG | TTATAGCACA | 1500 |
| GCCAAAGTAG | CATATACGAC | GACAACCACC | CGAGCAAGAA | GTAATTAAAA | AGAGACCAAC | 1560 |
| ACTTTTTAAA | TAAAATAAAT | TAGATATGAT | ATATTTAATT | ATAATTTCC | ATGGGGAAT | 1620 |
| CAATTACTAT | TATCATAATA | AAAATAAAAA | TAAAAATATT | GTTCTTGATT | TTATAATTTT | 1680 |
| TAAAATCTTA | AAGTAAAAGA | ATATATGAAA | GAGGACGTTG | ATTTGTTAAA | AGAAGATAGA | 1740 |
| TTATTATGGA | CGGTAAAACA | GTTCGGTATC | AAATAGACAT | AGAGATAGAC | ACGCGTATGA | 1800 |
| AAATAAGAAA | TAAGCATGGC | TTAGGTTGAA | AATAGTGCAG | CAAAGAAGGG | GTTATATATA | 1860 |
| TCCCTTCTTC | CCTCTCACAT | TAACTCATAT | CTCACTTCTG | TTCATAAAGA | GAAGGCACTG | 1920 |
| CAATGGACAA | CAAAGAGAAG | GAAGCCAGAG | AGAAATTAGG | AGGAGAAGTG | AAGCTCGGTC | 1980 |
| ATTGCTTGGA | TGTTATTTTG | AAGAATGCTG | ACGTAGCACT | GCACTATCCC | TCCTTCCTTA | 2040 |
| AGCTTTATGA | CCAACTTGTT | GCTGGGATCC | TCTTGAACAA | GGGAGCTATA | GTAAGTGCAA | 2100 |
| CCATATATAC | TTCAACTCAT | TTTACTCACC | TTTGTATATC | ATAACCATAT | TAAATCAGAA | 2160 |
| TATTGGCTTT | CTTTACTTTG | AATGCAGAAG | TACATCTTTG | ATAAGAAGTC | AAACAGCAAC | 2220 |
| TGGTACTTTA | TATTTGCAAG | AGCTCTCTCA | ATAGCTTGGA | TTGAAGATAA | GAGATACTGG | 2280 |
| AAATGGGGAT | CCTGGTATAA | TTTTTTAACT | AATTTCTCAA | GGGGAAAAAA | TGATAAGAAC | 2340 |
| TTGATTTCCT | GATCTCTCTC | ACTCGGGTGT | CTAAACACTT | GCAGTGGCGA | TAGCAACGTT | 2400 |
| GCAGAGCTTA | TTGAAGTATC | TTGGCTGGAC | ATTCGTGGAA | AGATCAACGA | GTCTATGCTC | 2460 |
| TCACAAAATG | TTGTGTATGA | GGTAGCACTT | CAGGTACAGC | TGAATAGTAG | AGCCTCCGGG | 2520 |
| TGGAATGCTC | CACTGAACAT | CGAGTTGAAG | AAGCCAGATG | GGAGCAAGAT | AGCGCGCCAG | 2580 |
| GAATGCCTGT | TGGGGAAGCC | ACAAAACCAG | TGGTTTGAGA | TTGTTGTTGA | GTTCAAGGTA | 2640 |
| GGCAACCATG | GCTGTGGAAG | TAGCGGCGAG | ATCGAGTTTG | CCTTTTTTGA | ACATGGAGGG | 2700 |
| CATTGGAAGA | GGGGGCTGCT | CGTGAAAGGC | GTTCGGATTG | GAGCAAAGGG | ATGTGGTTGC | 2760 |
| GCATGATCGA | AATCCTCTCT | CTCGAACTCA | GACTACACTT | ATTTTGATTT | TGAGAGGCCA | 2820 |
| GAGTTTGTGT | TATGATCCAA | TATGAAAAGA | ATGTACTAGC | TTGCAAACAT | AAATAACAGC | 2880 |
| ACCTTTTGCT | TACCGGCAAT | AAGGTCAAGT | TTTAAATACA | TTTTGTTTTA | GATACAATAA | 2940 |
| AATATACGTA | ATACTACTTT | TTTTTTGGTT | TACCAATCCG | GGTAAGTATA | AACACAGCAA | 3000 |
| ACAATTACGT | GAAACTCGTA | TTGGTTCTCA | TGCTTCACCG | ACTTTTGGCT | TACTA | 3055 |

( 2 ) INFORMATION FOR SEQ ID NO:2:

( i ) SEQUENCE CHARACTERISTICS:
        ( A ) LENGTH: 218 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

Met Asp Asn Lys Glu Lys Glu Ala Arg Glu Lys Leu Gly Gly Glu Val
   1           5             10             15

|     |     |     |     |     |     |     |     |     |     |     |     |     |     |     |     |
| --- | --- | --- | --- | --- | --- | --- | --- | --- | --- | --- | --- | --- | --- | --- | --- |
| Lys | Leu | Gly | His | Cys | Leu | Asp | Val | Ile | Leu | Lys | Asn | Ala | Asp | Val | Ala |
|     |     |     | 20  |     |     |     |     | 25  |     |     |     | 30  |     |     |     |
| Leu | His | Tyr | Pro | Ser | Phe | Leu | Lys | Leu | Tyr | Asp | Gln | Leu | Val | Ala | Gly |
|     |     | 35  |     |     |     |     | 40  |     |     |     |     | 45  |     |     |     |
| Ile | Leu | Leu | Asn | Lys | Gly | Ala | Ile | Lys | Tyr | Ile | Phe | Asp | Lys | Lys | Ser |
|     | 50  |     |     |     |     | 55  |     |     |     |     | 60  |     |     |     |     |
| Asn | Ser | Asn | Trp | Tyr | Phe | Ile | Phe | Ala | Arg | Ala | Leu | Ser | Ile | Ala | Trp |
| 65  |     |     |     |     | 70  |     |     |     |     | 75  |     |     |     |     | 80  |
| Ile | Glu | Asp | Lys | Arg | Tyr | Trp | Lys | Trp | Gly | Ser | Cys | Gly | Asp | Ser | Asn |
|     |     |     |     | 85  |     |     |     |     | 90  |     |     |     |     | 95  |     |
| Val | Ala | Glu | Leu | Ile | Glu | Val | Ser | Trp | Leu | Asp | Ile | Arg | Gly | Lys | Ile |
|     |     |     | 100 |     |     |     |     | 105 |     |     |     |     | 110 |     |     |
| Asn | Glu | Ser | Met | Leu | Ser | Gln | Asn | Val | Val | Tyr | Glu | Val | Ala | Leu | Gln |
|     |     |     | 115 |     |     |     |     | 120 |     |     |     |     | 125 |     |     |
| Val | Gln | Leu | Asn | Ser | Arg | Ala | Ser | Gly | Trp | Asn | Ala | Pro | Leu | Asn | Ile |
|     |     | 130 |     |     |     |     | 135 |     |     |     |     | 140 |     |     |     |
| Glu | Leu | Lys | Lys | Pro | Asp | Gly | Ser | Lys | Ile | Ala | Arg | Gln | Glu | Cys | Leu |
| 145 |     |     |     |     | 150 |     |     |     |     | 155 |     |     |     |     | 160 |
| Leu | Gly | Lys | Pro | Gln | Asn | Gln | Trp | Phe | Glu | Ile | Val | Val | Glu | Phe | Lys |
|     |     |     |     | 165 |     |     |     |     | 170 |     |     |     |     | 175 |     |
| Val | Gly | Asn | His | Gly | Cys | Gly | Ser | Ser | Gly | Glu | Ile | Glu | Phe | Ala | Phe |
|     |     |     | 180 |     |     |     |     | 185 |     |     |     |     | 190 |     |     |
| Phe | Glu | His | Gly | Gly | His | Trp | Lys | Arg | Gly | Leu | Leu | Val | Lys | Gly | Val |
|     |     | 195 |     |     |     |     | 200 |     |     |     |     | 205 |     |     |     |
| Arg | Ile | Gly | Ala | Lys | Gly | Cys | Gly | Cys | Ala |     |     |     |     |     |     |
|     | 210 |     |     |     |     | 215 |     |     |     |     |     |     |     |     |     |

( 2 ) INFORMATION FOR SEQ ID NO:3:

( i ) SEQUENCE CHARACTERISTICS:
        ( A ) LENGTH: 1151 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

| | | | | | |
|---|---|---|---|---|---|
| GATCTTTCTA | TTTAACTTTC | CTAAAGGAGA | AAGTATCAAA | CATCACATTA | TCCAAGAAAT | 60 |
| TTTTTTATAA | ATTCTAAGAT | TAAATTTATT | AAAAATAGAT | ATCCTTAAAA | ATCCATAGTC | 120 |
| TAAATAAAAC | TCAAGCGTTC | GAAGATGAGT | AAATAAATGT | GATTAATGTA | CAATATCGAC | 180 |
| GAATAAATAA | CGGTAGAAAA | AAATTATAAC | TTTCAACAAA | ATAACTGTTC | TAGTTTTATT | 240 |
| TTTTTCGTGT | GTCAAATAGA | TTTTTTATTT | AATATATATT | TTTAATTTA | TTAACGAACA | 300 |
| AAATATTATA | TTTAATTAAG | GTTTTAATTA | CAATATATGC | TATTTTCTAT | TAAAAAATGG | 360 |
| TTAATTATTT | TTCAAAACAC | AAATATAAAT | GAAAGGAAA | ATATATTTTT | TAAAAGAATT | 420 |
| AAAATGTCTT | TTCATTTCTT | TTACTTTTCT | TTTCGGGCAT | CATGAACCGA | AAATAATAGA | 480 |
| ACCTTCCTTT | TTAAGGCCTA | AATAGTTCAT | ATTCTAAATT | AAATTCGTGT | ATTCTTAGAT | 540 |
| TTATATAAAA | ATAAATTTCA | TAGACAAAAT | GCATTCATCC | ATACAAAATA | ATTAAAAACA | 600 |
| ACCGTTGGAT | TAATTCATTT | TCTTGAAGTA | GTAAAATCTT | TCAAAACTTC | TCTACGACGG | 660 |
| TAAAGTTAAA | ATGGAGTATT | GGGGGTCGAA | AAGGCAGGTT | GAGCAATTGC | AAGAACATCC | 720 |
| ATCTAGTTAT | AGCACAGCCA | AAGTAGCATA | TACGACGACA | ACCACCCGAG | CAAGAAGTAA | 780 |
| TTAAAAAGAG | ACCAACACTT | TTTAAATAAA | ATAAATTAGA | TATGATATAT | TTAATTATAA | 840 |

```
TTTTCCATGG GGGAATCAAT TACTATTATC ATAATAAAAA TAAAAATAAA AATATTGTTC      900

TTGATTTTAT AATTTTTAAA ATCTTAAAGT AAAAGAATAT ATGAAGAGG ACGTTGATTT       960

GTTAAAAGAA GATAGATTAT TATGGACGGT AAAACAGTTC GGTATCAAAT AGACATAGAG     1020

ATAGACACGC GTATGAAAAT AAGAAATAAG CATGGCTTAG GTTGAAAATA GTGCAGCAAA     1080

GAAGGGGTTA TATATATCCC TTCTTCCCTC TCACATTAAC TCATATCTCA CTTCTGTTCA     1140

TAAAGAGAAG G                                                         1151
```